United States Patent [19]

Shimono et al.

[11] Patent Number: 5,290,544
[45] Date of Patent: Mar. 1, 1994

[54] COSMETIC PRODUCTS CONTAINING A SOLUBLE GLASS

[75] Inventors: Fujio Shimono, Chita; Koichi Yamamoto, Nagoya; Toshiyuki Onishi, Ichinomiya; Ryota Miyoshi, Yono, all of Japan

[73] Assignee: Ishizuka Garasu Kabushiki Kaisha, Aichi, Japan

[21] Appl. No.: 838,692

[22] Filed: Feb. 21, 1992

[30] Foreign Application Priority Data

Feb. 22, 1991 [JP] Japan .................................. 3-114188

[51] Int. Cl.$^5$ ....................... A61K 7/027; A61K 7/035
[52] U.S. Cl. ......................................... 424/63; 424/69; 424/618
[58] Field of Search ................ 424/401, 618, 630, 69, 424/64

[56] References Cited

U.S. PATENT DOCUMENTS

| | | | |
|---|---|---|---|
| 1,642,089 | 9/1927 | Schreirer | 424/618 |
| 4,482,541 | 11/1984 | Telfer | 424/630 |
| 4,863,897 | 9/1989 | Dede | 424/630 |
| 5,009,898 | 4/1991 | Sakuma | 424/618 |
| 5,049,139 | 9/1991 | Gilchrist | 604/265 |
| 5,063,050 | 11/1991 | Verdon | 424/401 |

FOREIGN PATENT DOCUMENTS

| | | | |
|---|---|---|---|
| 032092 | 9/1985 | Japan | 424/630 |
| 238276 | 5/1986 | Japan | 424/618 |
| 457783 | 12/1936 | United Kingdom | 424/618 |

*Primary Examiner*—Thurman K. Page
*Assistant Examiner*—Sally Gardner
*Attorney, Agent, or Firm*—Townsend & Banta

[57] ABSTRACT

A cosmetic product is provided which comprises particles of soluble glass having an average particle size of 20 $\mu$m or less which contains silver ions. The soluble glass has a rate of elusion of the silver ions in water of from 0.00001-50 mg per hour per gram of glass when the soluble glass has a particle size of 420-600 $\mu$m and the water has a temperature of 20° C. The silver ions provide an anti-bacterial and anti-mold effect for a prolonged period without skin irritation, thus insuring a high degree of safety.

6 Claims, No Drawings

COSMETIC PRODUCTS CONTAINING A SOLUBLE GLASS

BACKGROUND OF THE INVENTION

The present invention relates to cosmetic products containing an inorganic antibacterial agent with a high safety, and more particularly to cosmetic products with no skin irritation which contain at least one of $Ag^-$, $Cu^-$, $Cu^{2-}$ and $Zn^{2-}$ having an antibacterial property.

In general, cosmetic products are used in the form of liquid, cream or powder. If the cosmetic products are contaminated by bacteria in the course of manufacture or usage, there is a possibility of skin trouble because the cosmetic products in any form are directly applied to a skin.

Conventionally, to prevent such bacterial contamination, raw materials of the cosmetic products are sterilized by an ethylene oxide gas, or an organic antibacterial agent such as para-oxybenzoic acid, salicyclic acid or dehydroacetic acid is employed in the cosmetic products.

Although the bacterial contamination of the cosmetic products can be prevented by the above measures, there occurs another problem such that persons with a delicate skin can suffer from the condition paraben allergy due to the above organic antibacterial agent.

To solve this problem, there has been proposed to use zeolite or the like carrying a silver compound or a metal ion. However, it is difficult to control the dissolving speed of the metal ion, and a long-term stable antibacterial effect cannot be obtained. Furthermore, the antimold effect is a weak, and color change by irradiation of light occurs.

SUMMARY OF THE INVENTION

It is accordingly an object of the present invention to provide cosmetic products which are not contaminated by bacteria and eliminate skin irritation to ensure a higher degree of safety.

The present inventors have accomplished the present invention in view of the traditional knowledge that a silver or copper vessel prevents rotting of food to ensure a high degree of safety.

According to the present invention, there is provided cosmetic products containing a soluble glass which contains at least one metal ion of $Ag^+$, $Cu^+$, $Cu^{2+}$ and $Zn^{2+}$ having an antibacterial property. Such a metal ion is gradually eluted into the cosmetic products to thereby realize a long-term stable antibacterial effect, and to also ensure a high degree of safety with no skin irritation.

The soluble glass to be used in the present invention is at least one of a borosilicate glass and a phosphate glass.

While glass is a durable material in general, it may be made soluble in water by weakening a network structure as the framework of the glass. The network structure of the glass may be weakened by increasing a content of the modifying oxide in the glass, or by increasing boric acid or phosphoric acid in the glass. The soluble glass of the present invention may be manufactured by any method used for ordinary glass. For example, a batch of glass material adjusted to a target composition may be heated to be vitrified. Alternatively, the soluble glass may be manufactured by a sol-gel method which has been recently developed. Thus, a manufacturing method for the soluble glass of the present invention is not particularly limited.

It is traditionally known that a silver or copper vessel for food can prevent rotting of the food. This is due to the fact that a very slight amount of silver or copper ion is eluted from the silver or copper vessel. It is said that about 20 $\mu g/l$ of silver in a solution indicates a bactericidal action. In general, a silver or copper ion in even a very slight amount can exhibit an action that is called "oligodynamic metal effect" to prevent the growing of fungi or the like. That is, such a metal ion is capable of being bonded to an activating enzyme center in a cell of bacterial or mold to exhibit a strong bactericidal action.

The dissolving or eluting speed of the metal ion, such as a silver ion or a copper ion as an antibacterial agent from the soluble glass into water, can be arbitrarily controlled. In the case of the silver ion, an eluting amount of the silver ion can be arbitrarily controlled in the range of 0.00001–50 mg per hour per gram of glass under the condition that a glass particle size is 420–600 $\mu m$ and the water temperature is 20° C. In the case of the copper ion, an eluting amount of the copper ion can be arbitrarily controlled in the range of 0.00001–300 mg per hour per gram of glass under the same condition as above.

The cosmetic products of the present invention contain the above-mentioned soluble glass containing an antibacterial agent, and exhibit an antibacterial effect and an antimold effect with a high degree of safety.

The safety of the cosmetic products of the present invention was tested as follows:

A primary skin irritation test was performed on a rabbit skin in accordance with the chemical substance toxicity test guide (1981) by OECD (Organization for Economic Corporation and Development), and it was proved that no irritation reaction was observed on the rabbit skin after exposure of a raw powder of the cosmetic products. Further, a test was performed on human skin in accordance with a method by the Japanese Industrial Skin Sanitary Association such that a raw powder bonded cloth was attached to the human skin, and it was proved that no trouble was observed on the human skin.

The cosmetic products of the present invention are preferably used as those containing water in a recipe, that is, liquid foundation, skin lotion, milky lotion, shampoo, hair rinse, etc.

The cosmetic products of the present invention may be those not containing water in the recipe, that is, powder foundation, eye shadow, lipstick, body powder, baby powder, etc. In this case, the effect of the present invention is sufficiently exhibited by making a composition of the soluble glass have a moisture absorbing property.

The cosmetic products of the present invention may be manufactured by pulverizing the soluble glass into a powder having an average particle size of about 20 $\mu m$ or less, preferably 5 $\mu m$ or less, adding the powder thus obtained into a recipe of the cosmetic products, and sufficiently mixing the whole. Further, in the case when the cosmetic products are those containing water in the recipe, such as liquid foundation, skin lotion, milky lotion, shampoo, hair rinse, etc., the cosmetic products may be manufactured by crushing the soluble glass into a bead having a particle size of about 2–10 mm., adding a desired amount of the bead into a vessel containing water in the recipe of the cosmetic products, and enclosing the bead in the vessel under the condition that the bead always contacts the water.

As described above, the cosmetic products of the present invention contains the soluble glass containing at least one metal ion of $Ag^+$, $Cu^+$, $Cu^{2+}$ and $Zn^{2+}$ as an antibacterial agent. Accordingly, such a metal ion is gradually eluted from the soluble glass into the cosmetic products to exhibit an antibacterial effect and an antimold effect for a long period of time. Moreover, no skin irritation occurs in the usage of the cosmetic products to ensure a high degree of safety.

Additional effects of the present invention are as follows:

An eluting amount of the metal ion contained in the soluble glass can arbitrarily be controlled by selecting a composition of the soluble glass.

It is not necessary to carry out a bactericidal process previously or successively by heating or with ethylene oxide gas. Accordingly, the manufacture of the cosmetic products can be greatly simplified.

DETAILED DESCRIPTION OF THE PREFERRED EMBODIMENTS

The present invention will be more clearly understood with reference to the following examples. In the following, "parts" represent parts by weight.

EXAMPLE 1

A talcum powder having the following composition was prepared.

| | |
|---|---|
| Talc (average particle size 15 μm) | 90.3 parts |
| Nylon 12 powder | 7.0 parts |
| Dimethylpolysiloxane (20 cs) | 2.0 parts |
| Silver ion containing soluble glass | 0.5 parts |
| Perfume | 0.2 parts |

The silver ion containing soluble glass used has the following conditions.

Theoretical glass composition:

$B_2O_3$ 45 mol %; $SiO_2$ 40 mol %; $Na_2O$ 15 mol %; $Ag_2O$ 0.5 wt %

Dissolving speed:

0.004 mg/g/Hr (silver ion eluting amount in water at 20° C. in a glass particle size of 425-600 μm)

Particle size: 10 μm or less

The above components were mixed together by using a henschel mixer, and the mixture obtained was pulverized by using an atomizer to obtain the intended talcum powder.

The talc used was unsterilized, and a standard plate count of bacteria and a mold count of the talcum powder obtained above and the talc used were measured in accordance with a pour-plate culture method to be used for a general cosmetic. The results of measurement are shown in Table 1.

TABLE 1

| | Standard plate count of bacteria | Mold count |
|---|---|---|
| Talcum powder | Negative/g | Negative/g |
| Talc | 500/g | 200/g |

This talcum powder was used with a puff twice a day under an ordinary condition, and the standard plate count of bacteria and the mold count were measured after six months. As the result, both the standard plate count and the mold count were negative, and no problems occurred.

EXAMPLE 2

A powder foundation composed of the following components 1 to 3 was prepared.

| | |
|---|---|
| Component 1: | |
| Silicone treated titanium dioxide | 10 parts |
| Silicone treated kaolin | 10 parts |
| Silicone treated sericite | 22 parts |
| Silicone treated mica | 20 parts |
| Silicone treated talc | 19 parts |
| Silicone treated iron oxide red | 0.3 parts |
| Silicone treated iron oxide yellow | 1.1 parts |
| Silicone treated iron oxide black | 0.1 parts |
| Nylon 12 powder | 5 parts |
| Component 2: | |
| Silver ion containing soluble glass | 0.5 parts |
| Component 3: | |
| Liquid paraffin | 5 parts |
| Isopropyl myristate | 5 parts |
| Methyl phenyl polysiloxane | 2 parts |

The silver ion containing soluble glass of the component 2 has the following conditions.

Theoretical glass composition:

$P_2O_5$ 50 mol %; CaO 44 mol %; $Al_2O_3$ 6 mol %; $Ag_2O$ 0.5 wt. %

Dissolving speed:

0.001 mg/g/Hr (silver ion eluting amount in water at 20° C. in a glass particle size of 425-600 μm)

Particle size: 10 μm or less

The silicone treated powder in the component 1 was prepared as follows:

Each subject powder to be treated (i.e., titanium dioxide, kaolin, sericite, mica, talc, iron oxide red, iron oxide yellow, and iron oxide black) was metered and mixed together by using a henschel mixer. Then, a dissolved mixture of 15 parts of xylene, 1.5 parts of methylhydrogen polysiloxane, and 1.5 parts of hydrogenated egg oil was added to 100 parts of the above powder mixture, and was mixed together again by using a henschel mixer. The mixture thus obtained was air-dried to remove the xylene, and was baked at 130° C. for 2 hours to obtain the silicone treated powder.

The components 1 and 2 were mixed together by using a henschel mixer, and the mixture thus obtained was pulverized by using an atomizer. Then, the component 3 heated was added to the above mixture of the components 1 and 2, and was mixed together by using a henschel mixer. Then, the mixture thus obtained was pulverized by using an atomizer. The powder thus obtained was filtered by a JIS 250 μm sieve, and was pressed to obtain the powder foundation.

To test a quality performance of the powder foundation (i.e., the product of Example 2), comparative samples of a powder foundation to be produced by a conventional method were prepared as follows:

Comparison 1

A powder foundation composed of the following components 1 to 3 was prepared.

| | |
|---|---|
| Component 1: | |
| Silicone treated titanium dioxide | 10 parts |
| Silicone treated kaolin | 10 parts |
| Silicone treated sericite | 22 parts |
| Silicone treated mica | 20 parts |

-continued

| | |
|---|---|
| Silicone treated talc | 19 parts |
| Silicone treated iron oxide red | 0.3 parts |
| Silicone treated iron oxide yellow | 1.1 parts |
| Silicone treated iron oxide black | 0.1 parts |
| Nylon 12 powder | 5 parts |
| Component 2: | |
| Methyl paraben | 0.2 parts |
| Butyl paraben | 0.2 parts |
| Sodium dehydroacetate | 0.1 parts |
| Component 3: | |
| Liquid paraffin | 5 parts |
| Isopropyl myristate | 5 parts |
| Methyl phenyl polysiloxane | 2 parts |

The silicone treated powder in the component 1 and the powder foundation were prepared by the same method as that in Example 2.

Comparison 2

A powder foundation composed of the following components 1 to 3 was prepared.

| | |
|---|---|
| Component 1: | |
| Silicone treated titanium dioxide | 10 parts |
| Silicone treated kaolin | 10 parts |
| Silicone treated sericite | 22.5 parts |
| Silicone treated mica | 20 parts |
| Silicone treated talc | 19 parts |
| Silicone treated iron oxide red | 0.3 parts |
| Silicone treated iron oxide yellow | 1.1 parts |
| Silicone treated iron oxide black | 0.1 parts |
| Nylon 12 powder | 5 parts |
| Component 2: | |
| Antibacterial agent | 0 parts |
| Component 3: | |
| Liquid paraffin | 5 parts |
| Isopropyl myristate | 5 parts |
| Methyl phenyl polysiloxane | 2 parts |

The silicone treated powder in the component 1 and the powder foundation were prepared by the same method as that in Example 2.

The powder foundations obtained in Example 2, Comparison 1 and Comparison 2 were used with a wet puff twice a day under an ordinary condition, and a standard plate count of bacteria and a mold count were measured after one month. The results of measurement are shown in Table 2.

TABLE 2

| | Standard plate count of bacteria | Mold count |
|---|---|---|
| Example 2 | Negative/g | Negative/g |
| Comparison 1 | Negative/g | Negative/g |
| Comparison 2 | $2 \times 10^4$/g | $2 \times 10^2$/g |

Further, a patch test of the powder foundations obtained in Example 2, Comparison 1 and Comparison 2 was carried out for 30 panelists. The result of the patch test is shown in Table 3.

TABLE 3

| | + | ± | − |
|---|---|---|---|
| Example 2 | 0 | 0 | 30 |
| Comparison 1 | 0 | 2 | 28 |
| Comparison 2 | 0 | 0 | 30 |

*criterion:
+ = complete erythema observed
± = partial erythema observed
− = no erythema observed It is understood from Table 3 that a so-called paraben allergy was just observed in Comparison 1.

EXAMPLE 3

An aqua face powder composed of the following components 1 to 5 was prepared.

| | |
|---|---|
| Component 1: | |
| Titanium dioxide | 3 parts |
| Zinc oxide | 5 parts |
| Mica | 10 parts |
| Talc | 10 parts |
| Iron oxide red | 0.7 parts |
| Iron oxide yellow | 1.1 parts |
| Iron oxide black | 0.2 parts |
| Component 2: | |
| Silver ion containing soluble glass | 0.5 parts |
| Component 3: | |
| Squalane | 10 parts |
| Component 4: | |
| Ethyl alcohol | 10 parts |
| Component 5: | |
| Glycerin | 1 parts |
| Purified water | 48.5 parts |

The silver ion containing soluble glass of the component 2 has the following conditions.

Theoretical glass composition:
$P_2O_5$ 50 mol %; MgO 44 mol %; $Al_2O_3$ 6 mol %; $Ag_2O$ 1.0 wt %

Dissolving speed:
0.0003 mg/g/Hr (silver ion eluting amount in water at 20° C. in a glass particle size of 425-600 μm)

Particle size: 5 μm or less

The components 1 and 2 were mixed together by using a henschel mixer, and the component 3 was sprayed to the mixture thus obtained to carry out further mixing. Then, the mixture was pulverized by using an atomizer.

The component 4 was added to the component 5 to carry out sufficient mixing. Then, the mixture of the components 1, 2 and 3 was added to the mixture of the components 4 and 5 to carry out uniform mixing, thereby obtaining the aqua face powder.

The talc used was unsterilized, and a standard plate count of bacteria and a mold count of the aqua face powder and the talc used were measured. The results of measurement are shown in Table 4.

TABLE 4

| | Standard plate count of bacteria | Mold count |
|---|---|---|
| Aqua face powder | Negative/g | Negative/g |
| Talc | 500/g | 200/g |

This aqua face powder was used with a puff twice a day under an ordinary condition, and the standard plate count of bacteria and the mold count were measured after six months. As the result, both the standard plate count and the mold count of the aqua face powder in Example 3 were negative, and no problems occurred.

EXAMPLE 4

An aqua face powder composed of the following components 1 to 5 was prepared.

| | |
|---|---|
| Component 1: | |
| Titanium dioxide | 3 parts |

| | |
|---|---|
| Zinc oxide | 5 parts |
| Mica | 10 parts |
| Talc | 8 parts |
| Iron oxide red | 0.7 parts |
| Iron oxide yellow | 1.1 parts |
| Iron oxide black | 0.2 parts |
| Component 2: | |
| Copper ion containing soluble glass | 2.5 parts |
| Component 3: | |
| Squalane | 10 parts |
| Component 4: | |
| Ethyl alcohol | 10 parts |
| Component 5: | |
| Glycerin | 1 parts |
| Purified water | 48.5 parts |

The copper ion containing soluble glass of the component 2 has the following conditions.

Theoretical glass composition:

$P_2O_5$ 60 mol %; $K_2O$ 20 mol %; CaO 15 mol %; CuO 5.0 mol %

Dissolving speed:

0.002 mg/g/Hr (copper ion eluting amount in water at 20° C. in a glass particle size of 425–600 μm)

Particle size: 10 μm or less

The components 1 and 2 were mixed together by using a henschel mixer, and the component 3 was sprayed to the mixture thus obtained to carry out further mixing. Then, the mixture was pulverized by using an atomizer.

The component 4 was added to the component 5 to carry out sufficient mixing. Then, the mixture of the components 1, 2 and 3 was added to the mixture of the components 4 and 5 to carry out uniform mixing, thereby obtaining the aqua face powder.

The talc used was unsterilized, and a standard plate count of bacteria and a mold count of the aqua face powder and the talc used were measured. The results of measurement are shown in Table 5.

TABLE 5

| | Standard plate count of bacteria | Mold count |
|---|---|---|
| Aqua face powder | Negative/g | Negative/g |
| Talc | 500/g | 200/g |

This aqua face powder was used with a puff twice a day under an ordinary condition, and the standard plate count of bacteria and the mold count were measured after six months. As the result, both the standard plate count and the mold count of the aqua face powder in Example 3 were negative, and no problems occurred.

What is claimed is:

1. Cosmetic products comprising a cosmetic base and particles of a soluble glass having an average particle size of 20 μm or less, said soluble glass comprising Ag+, and having a rate of eluting of said Ag+ in water of from about 0.00001–50 mg per hour per gram of glass on the condition that the soluble glass has a particle size of 420–600 μm and the water has a temperature of 20° C., wherein said cosmetic base comprises a solid material free from water, which is selected from the group consisting of powder foundation, eye shadow, lipstick, body powder and baby powder, and said soluble glass comprises a moisture absorbing substance.

2. Cosmetic products as defines in claim 1, wherein said moisture absorbing substance is selected from the group consisting of a boric acid, phosphoric acid and alkali.

3. Cosmetic products as defined in claim 1, wherein said soluble glass comprises $B_2O_3$, $SiO_2$, $Na_2O$ and $Ag_2O$.

4. Cosmetic products as defined in claim 1, wherein said soluble glass comprises $P_2O_5$, CaO, $Al_2O_3$ and $Ag_2O$.

5. Cosmetic products as defined in claim 1, wherein said soluble glass comprises $P_2O_5$, MgO, $Al_2O_3$ and $Ag_2O$.

6. Cosmetic products as defined in claim 1, wherein said soluble glass comprises $P_2O_5$, $K_2O$, CaO and CuO.

* * * * *